United States Patent [19]

Desmurs et al.

[11] Patent Number: 5,563,274
[45] Date of Patent: Oct. 8, 1996

[54] PROCESS OF PREPARING OPTICALLY ACTIVE ALPHA-CHLOROCARBOXYLIC ESTERS

[75] Inventors: Jean-Roger Desmurs, Saint Symphorien D'Ozon; Pascal Metivier, Lyons; Genevieve Padilla, Solaize; Harivelo Rajoharison, Echirolles, all of France

[73] Assignee: Rhone-Poulenc Chimie, Courbevoie, France

[21] Appl. No.: 161,098

[22] Filed: Dec. 3, 1993

Related U.S. Application Data

[63] Continuation of Ser. No. 870,757, Apr. 20, 1992, abandoned, which is a continuation of Ser. No. 468,850, Jan. 23, 1990, abandoned.

[30] Foreign Application Priority Data

Jan. 23, 1989 [FR] France .................................. 89 00983

[51] Int. Cl.$^6$ ..................... C07C 69/63; C07D 213/63; C07D 307/58; C07D 335/02
[52] U.S. Cl. ..................... 546/303; 549/420; 549/479; 560/226
[58] Field of Search ..................... 546/303; 560/226; 549/420, 479

[56] References Cited

FOREIGN PATENT DOCUMENTS

| 0163435 | 12/1985 | European Pat. Off. | ............... 560/226 |
|---|---|---|---|
| 2459221 | 1/1981 | France | .................................. 560/226 |
| 1135893 | 9/1962 | Germany | .............................. 570/193 |

OTHER PUBLICATIONS

Andrew Streitweser, Jr. and Clayton H. Heathcock, Introduction To Organic Chemistry, p. 69 (1976).
N. Irving Sax and Richard J. Lewis, Sr., Hawley's Condensed Chemical Dictionary, pp. 53, 100, 680, 898, 1148 and 1209. (1987).
Crosby et al., Chem. Abstracts, vol. 105, No. 13, Abst. No. 114,607–V, Sep. 29, 1986.

*Primary Examiner*—Alan L. Rotman
*Attorney, Agent, or Firm*—Finnegan, Henderson, Farabow, Garrett & Dunner, L.L.P.

[57] ABSTRACT

A process of preparing optically active alpha-chlorocarboxylic esters having the formula:

$$R-\underset{Cl}{CH}-COOR_1 \qquad (I)$$

from an optically active alpha-hydroxy carboxylic ester having the formula:

$$R-\underset{OH}{CH}-COOR_1 \qquad (II)$$

in which process, an alpha-hydroxy carboxylate of formula II is brought into contact with phosgene and a compound chosen from amides, lactams and ureas, wherein $R_1$ is an optionally substituted hydrocarbyl residue and R is preferably a methyl group.

23 Claims, No Drawings

PROCESS OF PREPARING OPTICALLY ACTIVE ALPHA-CHLOROCARBOXYLIC ESTERS

This application is a continuation of application Ser. No. 07/870,757 filed Apr. 20, 1992, now abandoned, which was a continuation of application Ser. No. 07/468,850, filed Jan. 23, 1990, abandoned.

FIELD OF THE INVENTION

The present invention relates to a process of preparing optically active alpha-chlorocarboxylic esters, such as esters of 2-chloropropionic acid, from the corresponding optically active alpha-carboxylic esters such as lactic esters.

BACKGROUND OF THE INVENTION

Optically active esters of 2-chloropropionic acid are known chemical intermediates which are used to obtain chemical products useful in the agrochemical industry, particularly in the field of herbicides. Optically active herbicides are advantageous because they are active in dosages which are smaller by one-half than corresponding racemic compounds, thus lessening environmental concerns.

Several processes have already been proposed in order to achieve the synthesis of optically active esters of 2-chloropropionic acid having the highest yields possible.

For example, French Patent FR-B-2,459,221 describes a two-step process wherein, in a first stage, a racemic or optically active alkyl lactic ester is chlorinated in the presence of thionyl chloride and an organic base and then, in a second stage, the reaction mixture resulting from the first stage is heated to a temperature which is at least equal to the decomposition temperature of the alkyl lactate chlorosulfite. In the first stage, a molar excess of thionyl chloride of at least 2.5% relative to the quantity of alkyl lactate introduced into the mixture is maintained, while maintaining a temperature below the decomposition temperature of the alkyl lactate chlorosulfite. European Published Patent Application EP-A-0,163,435 describes the chlorination of alkyl lactate using phosgene in the presence of a tertiary amine. This reaction takes place via a chloroformate intermediate of the formula $CH_3$—$CH(OCOCl)$—$CO_2R$, which is then decomposed. However, the disclosed process requires the use and subsequent removal of a large, stoichiometric, quantity of amine. Furthermore, the disclosed process requires a large excess of $COCl_2$.

German Published Patent Application DE-A-1,135,893 discloses reacting 1-butyn-3-ol with excess phosgene in the presence of approximately 10% of dimethylformamide at a temperature of between 50° and 55° C. to produce the corresponding chlorine compound in a 79% yield. However, because the disclosed process is concerned with racemic compounds, there is no teaching with regard to optical isomerism.

To meet present day requirements, a first objective of the present invention is to provide a process wherein, by starting from an optically active corresponding alpha-carboxylic ester, such as a lactic acid ester, an alpha-chlorocarboxylic ester, such as an ester of 2-chloropropionic acid, may be obtained in an excellent yield, while preserving an excellent optical activity (optical yield).

Another objective of the invention is to provide a process which is simpler than the prior art, especially with respect to the retreatment stage.

SUMMARY OF THE INVENTION

The present invention relates to a process of preparing an optically active alpha-chlorocarboxylic ester from the corresponding alpha-hydroxy carboxylate with phosgene and a compound selected from the group consisting of amides, lactams and substituted ureas.

Preferably, the optically active alpha-chlorocarboxylate has the formula:

and the corresponding alpha-hydroxy carboxylate has the formula:

wherein R and $R_1$ are independently selected substituted or unsubstituted hydrocarbyl residues.

R and $R_1$ are both independently chosen, preferably, from the following radicals: linear or branched $C_1$-$C_{18}$ alkyl, more preferably $C_1$-$C_{12}$; linear or branched $C_2$-$C_{18}$ alkenyl, more preferably $C_2$-$C_{12}$; linear or branched $C_2$-$C_{18}$ alkynyl, more preferably $C_2$-$C_{12}$; linear or branched $C_3$-$C_{18}$ cycloalkyl, more preferably $C_3$-$C_{12}$; linear or branched $C_6$-$C_{14}$ aryl, more preferably $C_6$-$C_{10}$; and linear or branched $C_7$-$C_{15}$ aralkyl, more preferably $C_7$-$C_{11}$.

Preferably, R is a lower alkyl ($C_1$-$C_6$) or a lower aralkyl ($C_7$-$C_{11}$) radical. Most preferably, R is a methyl group so that formula II corresponds to a lactate. $R_1$ is preferably a $C_1$-$C_6$ alkyl radical.

The above-mentioned radicals may be substituted by one or more halogen atoms or by a $C_1$-$C_6$ alkoxy or alkylthio radical. In the case of aryl or aralkyl radicals, one to four carbon atoms may be replaced by one to four hetero atoms respectively, chosen from the group consisting of oxygen, sulfur and nitrogen atoms. Furyl, thiophenyl and pyridyl are exemplary of suitable substituted radicals.

Amides which may be employed according to the process of the present invention include aliphatic amides and those corresponding to the formula:

wherein $R_2$ is a hydrogen atom or a $C_1$-$C_6$ alkyl or $C_3$-$C_{10}$ cycloalkyl radical, and $R_3$ and $R_4$, which are identical or different, are a $C_1$-$C_6$ alkyl or $C_3$-$C_{10}$ cycloalkyl radical. In the case that $R_2$ is a $C_1$-$C_6$ alkyl radical or a $C_3$-$C_{10}$ cycloalkyl radical, one to three carbon atoms of the radical may be replaced by one to three hetero atoms chosen from among oxygen, sulfur and nitrogen atoms. Similarly, one to three carbons of the radicals $R_3$ and $R_4$ may be replaced by one to three hetero atoms chosen from among oxygen, sulfur and nitrogen atoms.

N,N-dimethylformamide and N,N-dimethylacetamide are exemplary of the amides which are suitable for the process of the present invention.

Lactams which may be employed according to the process of the present invention include those corresponding to the formula:

wherein $R_5$ is a $C_1$-$C_6$ alkyl or $C_3$-$C_{10}$ cycloalkyl radical and $R_6$ is a $C_2$-$C_{10}$ alkylene group. One to three carbons of the $R_5$ and $R_6$ radicals may be replaced by one to three hetero atoms chosen from among oxygen, sulfur and nitrogen atoms.

N-methylpyrrolidinone is exemplary of a lactam which is suitable for the process of the present invention.

The ureas which may be employed in the process according to the present invention include those corresponding to the formula:

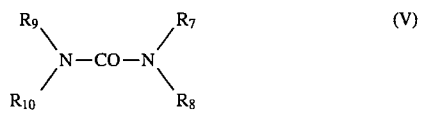

wherein $R_7$, $R_8$, $R_9$ and $R_{10}$, which are identical or different, denote a hydrogen atom or a $C_1$-$C_{10}$ radical, preferably a $C_1$-$C_6$ alkyl or $C_3$-$C_{10}$ cycloalkyl radical. One to three carbon atoms of $R_7$, $R_8$, $R_9$ and $R_{10}$ may be replaced by one to three hetero atoms respectively, chosen from oxygen, sulfur and nitrogen atoms. Tetramethylurea is exemplary of a urea suitable for the process of the present invention.

Amides and lactams are the preferable compounds to be used in the process according to the present invention.

The process according to the present invention may be carried out in bulk without any additional solvent other than the reactants and the final products themselves. Indeed, the final products of alpha-chlorocarboxylic esters are very good solvents. 2-Chloropropionate provides particularly satisfactory results as a solvent. Therefore, the process according to the present invention may be carried out in a system wherein the reactants are continuously introduced into the system while bleeding off the final product, a portion of which is then used as a solvent in the process.

The process according to the present invention may also be carried out in the presence of a solvent medium, preferably an aprotic solvent. Aprotic solvents useful in the present invention include: saturated aliphatic hydrocarbons such as n-pentane, isopentane, 2-methylhexane, and 2,2,5-trimethylhexane; aromatic hydrocarbons such as benzene, toluene and ethylbenzene; saturated aliphatic ethers such as tetrahydrofuran and isopentyl ether; aromatic ethers such as benzethyl ether; aromatic or saturated aliphatic ketones such as methyl ethyl ketone, methyl isobutyl ketone and acetophenone; aromatic or aliphatic saturated halogenated hydrocarbons such as mono- or polyhalobenzene, 1-chloro- 2-methylpropane and isobutyl chloride; and aromatic or saturated aliphatic esters such as isobutyl, ethyl acetate and methyl benzoate. All of the above-mentioned solvents may be present by themselves or in combinations.

Aromatic hydrocarbons, whether halogenated or not, are the preferable solvents to be used in the present invention. If the process is carried out in the presence of a solvent, the dilution of the reaction product will be preferably between about 0.5% and about 99% by weight relative to the total weight of the solution, and preferably between about 5 and about 50%.

In a preferred embodiment, the solvent medium used in the invention comprises alpha-chlorocarboxylate obtained by the claimed process. Even more preferably, the process is continuously carried out in a system wherein the reactants are continuously introduced into the system while bleeding off the final product, a portion of which is then used as the solvent medium.

The molar proportion of $COCl_2$ relative to the alpha-hydroxy carboxylate may vary over a considerable range, although a person skilled in the art will readily understand that the $COCl_2$/alpha-hydroxy carboxylate ratio is at least close to about 1 in order that the reaction may be complete. A $COCl_2$/alpha-hydroxy carboxylate molar ratio of between about 0.9 and about 3 is preferred. A molar ratio of between about 0.95 and about 1.5 is even more preferred, and a molar ratio of between about 1 and about 1.2 is the most preferred. Insofar as the amides, lactams and ureas are concerned, the quantity employed will be such that the molar ratio relative to $COCl_2$ will be between about 1/100 and about 1/2, preferably lower than about 1/5. The reaction temperature is advantageously between about 0° C. and about 100° C.

According to another advantageous embodiment, by using a solvent and an amide, urea or lactam with a boiling point which is high relative to the $C_1$-$C_3$ alkyl chloropropionate obtained, the recovery of the solvent and the amide, lactam or urea at the foot of the reactor and the recycling of the latter may be achieved.

The following examples illustrate the process according to the present invention. However, these examples are illustrative and are not meant to limit the present invention.

EXAMPLE 1

Chlorination of Methyl Lactate with $COCl_2$ in the Presence of DMF 30 ml of chlorobenzene, 6.05 g (58.2 mmol) of r-(+) methyl lactate (96.7% optical purity) and 450 μl of dimethylformamide were charged into a 50-ml three-necked flask. The mixture was heated to 80° C. and 6.32 g (63.8 mmol) of $COCl_2$ were then added at this temperature during 1.33 hours. The reaction mixture was kept at 80° C. for 1 hour and was then cooled rapidly to ambient temperature.

A dark red crude reaction mixture was obtained which contained 6.6 g of S-(−)methyl chloropropionate (92.5% yield), according to a determination by vapor phase chromatography in the presence of 1,2-dichlorobenzene as an internal standard.

This reaction mixture was hydrolyzed using 20 ml of water. The aqueous phase was separated by gravity and then washed once with $CH_2Cl_2$. The combined organic layers were washed three times with water and then dried over $Na_2SO_4$ overnight.

An aliquot portion of the combined organic phase was taken and then distilled under vacuum. The fraction which distilled at 33° C./30 mbar was removed. Analysis of this last fraction by vapor phase chromatography, with the aid of a chiral column, showed that the S-(−)methyl chloropropionate obtained contained 3.2% of the dextrorotatory enantiomer, R-(+)methyl chloropropionate (optical yield=100%).

EXAMPLE 2

Chlorination of Isobutyl Lactate Using $COCl_2$ in the Presence of DMF 30 ml of chlorobenzene, 9.36 g (64.1 mmol) of R-(+) isobutyl lactate ($\alpha_D$=+14.1, 97.9% optical purity) and 490 μl of dimethylformamide were charged into a 50-ml three-necked flask. The mixture was heated to 80° C., and 6.98 g (70.5 mmol) of $COCl_2$ were then added at this temperature during 2.83 hours. The reaction mixture was kept at 80° C. for 1 hour and was then cooled rapidly to ambient temperature.

A dark yellow orange crude reaction mixture was obtained which contained 9.44 g of S-(−) isobutyl chloropropionate (90% yield), according to a determination by vapor phase chromatography in the presence of 1,2-dichlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature, and the dichlorobenzene was removed at 29° C. at 22 mbar. The head fraction which distilled between 20° C. and 43.5° C. at 5 mbar was removed, and the main fraction which distilled at 44°–45.5° C. at 5 mbar was analyzed by vapor phase chromatography on a column containing a chiral stationary phase. This analysis showed that the S-(−) isobutyl chloropropionate obtained contained 2.9% of the dextrorotatory enantiomer (R-(+)isobutyl chloropropionate). (Optical yield=96%).

EXAMPLE 3

Chlorination of Isobutyl Lactate Using $COCl_2$ in the Presence of DMF 30 ml of chlorobenzene and 470 μl of dimethylformamide were charged into a 50-ml three-necked flask. The mixture was heated to 80° C., and 8.82 g (60.4 mmol) of R-(+)isobutyl lactate and 6.66 g (67.3 mmol) of $COCl_2$ were added in parallel at this temperature during 1.17 hours. The reaction mixture was kept at 80° C. for 1 hour and was then cooled rapidly to ambient temperature.

A dark yellow orange crude reaction mixture was obtained which contained 9.54 g of S-(−)isobutyl chloropropionate (96% yield), according to a determination by vapor phase chromatography in the presence of 1,2-dichlorobenzene as an internal standard.

This reaction mixture was hydrolyzed using 20 ml of water. The aqueous phase was separated by gravity and then washed once with $CH_2Cl_2$. The combined organic layers were washed twice with water and were then dried over $Na_2SO_4$ overnight.

The dichloromethane was stripped off under vacuum at ambient temperature, and the chlorobenzene was removed at 29° C. at 22 mbar. The head fraction which distilled between 20° C. and 43.5° C. at 5 mbar was removed, and the main fraction which distilled at 44°–45.5° C. at 5 mbar was analyzed by vapor phase chromatography on a column containing a chiral stationary phase. This analysis showed that the S-(−)-isobutyl chloropropionate obtained contained 2.7% of the dextrorotatory enantiomer (R-(+)isobutyl chloropropionate). (Optical yield=99%).

EXAMPLE 4

Chlorination of Isobutyl Lactate Using $COCl_2$ in the Presence of DMF 30 ml of 1,2,4-trichlorobenzene and 480 μl of dimethylformamide were charged into a 50-ml three-necked flask. The mixture was heated to 80° C., and 9.01 g (61.7 mmol) of R-(+)isobutyl lactate and 6.86 g (67.3 mmol) of $COCl_2$ were then added in parallel at this temperature during one hour. The reaction mixture was kept at 80° C. for one hour and was then cooled rapidly to ambient temperature.

A dark yellow orange crude reaction mixture is was obtained which contained 9.23 g of S-(−)isobutyl chloropropionate (91% yield), according to a determination by vapor phase chromatography in the presence of chlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature. The head fraction which distilled between 20° C. and 43.5° C. at 5 mbar was removed, and the main fraction which distilled at 44°–45.5° C. at 5 mbar was analyzed by vapor phase chromatography on a column containing a chiral stationary phase. This analysis showed that the S-(−)isobutyl chloropropionate obtained contained 2.7% of the dextrorotatory enantiomer (R-(+)isobutyl chloropropionate). (Optical yield=99%).

EXAMPLE 5

Chlorination of Isobutyl Lactate Using $COCl_2$ in the Presence of N,N-Dibutylformamide 28 ml of 1,2,4-trichlorobenzene and 1.05 ml of dibutylformamide were charged into a 50-ml three-necked flask. The mixture was heated to 80° C. and 8.39 g (57.5 mmol) of R(+)isobutyl lactate and 6.26 g (63.2 mmol) of $COCl_2$ were then added in parallel at this temperature during one hour. The reaction mixture was kept at 80° C. for one hour and was then cooled rapidly to ambient temperature.

A dark red brown crude reaction mixture was obtained which contained 8.74 g of S-(−)isobutyl chloropropionate (92% yield), according to a determination by vapor phase chromatography in the presence of chlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature. The head fraction which distilled between 20° C. and 43.5° C. at 5 mbar was removed, and the main fraction which distilled at 44°–45.5° C. at 5 mbar was analyzed by vapor phase chromatography on a column containing a chiral stationary phase. This analysis showed that the S-(−)isobutyl chloropropionate obtained contained 2.9% of the dextrorotatory enantiomer (R-(+)isobutyl chloropropionate). (Optical yield=98%).

EXAMPLE 6

Chlorination of Isobutyl Lactate Using $COCl_2$ in the Presence of DMAC (Addition of Phosgene to a Solution of Lactate+DMAC+Solvent)

30 ml of chlorobenzene, 8.74 g (60 mmol) of R-(+) isobutyl. lactate ($\alpha_D$=+14.1, 97.9% optical purity) and 550 μl of dimethylacetamide were charged into a 50-ml three-necked flask. The mixture was heated to 80° C., and 6.52 g (65.8 mmol) of $COCl_2$ were then added at this temperature during 1.15 hour. The reaction mixture was kept at 80° C. for 1 hour and was then cooled rapidly ambient temperature.

A dark yellow orange crude reaction mixture was obtained which contained 4.20 g of S-(−)isobutyl chloropropionate (43.3% yield), according to a determination by vapor phase chromatography in the presence of 1,2-dichlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature, and the chlorobenzene was removed at 29° C. at 22 mbar. The head fraction which distilled between 20° C. and 43.5° C. at 5 mbar was removed, and the main fraction which distilled at 44°–45.5° C. at 4 mbar was analyzed by vapor phase chromatography on a column containing a chiral stationary phase. This analysis showed that the S-(–)isobutyl chloropropionate obtained contained 3.5% of the dextrorotatory enantiomer (R-(+)isobutyl chloropropionate). (Optical yield=97%).

EXAMPLE 7

Chlorination of Isobutyl Lactate Using $COCl_2$ in the Presence of NMP (Addition of Phosgene to a Solution of Lactate+NMP+Solvent).

30 ml of chlorobenzene, 9.1 g (62.3 mmol) of R-(+)isobutyl lactate ($\alpha_D$=+14.1, 97.9% optical purity) and 600 µl of N-methylpyrrolidone were charged into a 50-ml three-necked flask. The mixture was heated to 80° C., and 6.79 g (69 mmol) of $COCl_2$ were then added at this temperature during 1.15 hour. The reaction mixture was kept at 80° C. for 1 hour and was then cooled rapidly to ambient temperature.

A dark yellow orange crude reaction mixture was obtained which contained 7.21 g of S-(–)isobutyl chloropropionate (70% yield), according to a determination by vapor phase chromatography in the presence of 1,2-dichlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature, and the chlorobenzene was removed at 29° C. at 22 mbar. The head fraction which distilled between 20° C. and 43.5° C. at 5 mbar was removed, and the main fraction which distilled at 44°–45.5° C. at 4 mbar was analyzed by vapor phase chromatography on a column containing a chiral stationary phase. This analysis showed that the S-(–)isobutyl chloropropionate obtained contained 2.3% of the dextrorotatory enantiomer (R-(+)isobutyl chloropropionate). (Optical yield=99%).

EXAMPLE 8

Chlorination of Isobutyl Lactate Using $COCl_2$ in the Presence of TMU (Addition of Phosgene to a Solution of Lactate+TMU+Solvent)

30 ml of chlorobenzene, 10.95 (75 mmol) of R-(+)isobutyl lactate ($\alpha_D$=+14.1, 97.9% optical purity) and 900 µl of tetramethylurea (TMU) were charged into a 50-ml three-necked flask. The mixture was heated to 80° C., and 8.17 g (82.5 mmol) of $COCl_2$ were then added at this temperature during 1.5 hour. The reaction mixture was kept at 80° C. for one hour and was then cooled rapidly to ambient temperature.

A dark yellow orange crude reaction mixture was obtained which contained 1.66 g of S-(–)isobutyl chloropropionate (13.4% yield), according to a determination by vapor phase chromatography in the presence of 1,2-dichlorobenzene as an internal standard.

This reaction mixture was hydrolyzed using 20 ml of water. The aqueous phase was separated by gravity and was then washed once with $CH_2Cl_2$. The combined organic layers were washed twice with water and were then dried over $Na_2SO_4$ overnight.

The dichloromethane was stripped off under vacuum at ambient temperature, and the chlorobenzene was removed at 29° C. at 22 mbar. The head fraction which distilled between 20° C. and 43.5° C. at 5 mbar was removed, and the main fraction which distilled at 44°–45.5° C. at 4 mbar was analyzed by vapor phase chromatography on a column containing a chiral stationary phase. This analysis showed that the S-(–)isobutyl chloropropionate obtained contained 5.9% of the dextrorotatory enantiomer (R-(+)isobutyl chloropropionate). (Optical yield=92%).

EXAMPLE 9

Chlorination of Isobutyl Lactate Using $COCl_2$ in the Presence of N-Formylmorpholine 30 ml of 1,2,4-trichlorobenzene and 0.86 ml of N-formylmorpholine were charged into a 50-ml three-necked flask. The mixture was heated to 80° C., and 12.54 g (85.9 mmol) of R(+)isobutyl lactate and 9.34 g (94.3 mmol) of $COCl_2$ were then added in parallel at this temperature during 1.05 hour. The reaction mixture was kept at 80° C. for one hour and was then cooled rapidly to ambient temperature.

A dark yellow orange crude reaction mixture was obtained which contained 11.78 g of S-(–)isobutyl chloropropionate (96% yield), according to a determination by vapor phase chromatography in the presence of 1,2-dichlorobenzene as an internal standard.

A fraction of the reaction mixture was distilled under vacuum. The head fraction which distilled between 20° C. and 43.5° C. at 5 mbar was removed, and the main fraction which distilled at 44°–45.5° C. at 5 mbar was analyzed by vapor phase chromatography on a column containing a chiral stationary phase. This analysis showed that the S-(–) isobutyl chloropropionate obtained contained 3.3% of the dextrorotatory enantiomer (R-(+)isobutyl chloropropionate). (Optical yield=98%).

What is claimed is:

1. A process of preparing an optically active alpha chlorocarboxylate ester from the corresponding alpha hydroxy carboxylate, which comprises reacting an alpha hydroxy carboxylate with phosgene and a compound selected from the group consisting of amides, lactams and substituted ureas wherein the molar ratio of phosgene to alpha-hydroxy carboxylate is between about 0.9 and about 3, and the molar ratio of said compound to phosgene is between about 1/100 and about ½ at a temperature of greater than 40° C. to about 100° C. for a time sufficient to obtain said optically active alpha chlorocarboxylate ester.

2. A process of preparing an optically active alpha chlorocarboxylate ester according to claim 1, wherein the obtained optically active alpha-chlorocarboxylate has the formula:

and said alpha-hydroxy carboxylate has the formula:

wherein R and $R_1$ are independently selected from the group consisting of linear or branched $C_1$-$C_{18}$ alkyl radicals, linear or branched $C_2$-$C18$ alkenyl radicals, linear or branched $C_2$-$C_{18}$ alkynyl radicals, linear or branched $C_3$-$C_{18}$ cycloalkyl radicals, linear or branched $C_6$-$C_{14}$ aryl radicals, and linear or branched $C_7$-$C_{15}$ aralykl radicals, furyl, thiophenyl and pyridyl radicals.

3. A process of preparing an optically active alpha-chlorocarboxylate ester according to claim 2, wherein $R_1$ is substituted by one or more halogen atoms or by a $C_1$-$C_6$ alkoxy or alkylthio radical and R is a $C_1$-$C_6$ low alkyl or a $C_7$-$C_{11}$ lower aralkyl.

4. A process of preparing an optically active alpha-chlorocarboxylate ester according to claim 2, wherein R is methyl.

5. A process of preparing an optically active alpha-chlorocarboxylate ester according to claim 2, wherein $R_1$ is a $C_1$-$C_6$ alkyl radical.

6. A process of preparing an optically active alpha-chlorocarboxylate ester according to claim 2, wherein said compound selected from the group consisting of amides, lactams and substituted ureas, is an amide having the formula:

$$R_2-CO-NR_3R_4 \qquad (III)$$

wherein,
$R_2$ is selected from the group consisting of a hydrogen atom, a $C_1$-$C_6$ alkyl radical and a $C_3$-$C_{10}$ cycloalkyl radical, and $R_3$ and $R_4$, which are identical or different, are selected from the group consisting of $C_1$-$C_6$ alkyl radicals and $C_3$-$C_{10}$ cycloalkyl radicals.

7. A process of preparing an optically active alpha-chlorocarboxylate ester according to claim 2, wherein said contacting is carried out in a solvent medium.

8. A process of preparing an optically active alpha-chlorocarboxylate ester according to claim 7, wherein said solvent medium is a halogenated or unhalogenated aromatic solvent.

9. A process of preparing an optically active alpha-chlorocarboxylate ester according to claim 7, wherein said solvent medium comprises alpha-chlorocarboxylate obtained by the claimed process.

10. A process of preparing an optically active alpha-chlorocarboxylate ester according to claim 9, wherein said process is continuously carried out in a system wherein the reactants are continuously introduced into the system while bleeding off the final product, a portion of which is then used as said solvent medium.

11. A process of preparing an optically active alpha chlorocarboxylate ester according to claim 10, wherein the molar ratio of said compound to $COCl_2$ is lower than ⅕.

12. A process of preparing an optically active alpha chlorocarboxylate ester according to claim 1, wherein said compound is selected from lactams and substituted ureas.

13. The process of claim 1 which is carried out for a time and at a temperature sufficient to obtain said optically active alpha chlorocarboxylate ester in an optical yield of at least 92%.

14. The process of claim 1, wherein said process is carried out in a single step.

15. The process of claim 1, wherein said process is carried out at a reaction temperature of about 80° C.

16. The process of claim 1, wherein the molar ratio of phosgene to alpha-hydroxy carboxylate is between about 0.9 and about 1.5, and the molar ratio of said compound to phosgene ranges from 1/100 to ⅕.

17. The process of claim 1, wherein the molar ratio of phosgene to alpha-hydroxy carboxylate is between about 0.95 and about 1.5.

18. The process of claim 1, wherein the molar ratio of said compound to phosgene is lower than about ⅕.

19. The process of claim 1, wherein said process is carried out at a reaction temperature of about 60° C.

20. The process of claim 1, wherein said amides are N-N-dimethylethyl or N,N-dimethylacetamide.

21. The process of claim 1, wherein said lactams are N-methylpyrrolidinone.

22. The process of claim 1, wherein said ureas are tetramethylurea.

23. A process of preparing an optically active alpha-chlorocarboxylate ester according to claim 2, wherein $R_1$ is selected from the group consisting of furyl, thiophenyl and pyridyl radicals.

* * * * *

UNITED STATES PATENT AND TRADEMARK OFFICE
CERTIFICATE OF CORRECTION

PATENT NO. : 5,563,274
DATED : October 8, 1996
INVENTOR(S) : Jean-Roger DESMURS et al.

It is certified that error appears in the above-indentified patent and that said Letters Patent is hereby corrected as shown below:

Title Page Column 1, Item [75], Inventors, line 3, "Lyons" should read --Lyon--.

Claim 2, Column 8, line 63, $C_2$-C18" should read --$C_2$-$C_{18}$--.

Claim 2, Column 8, line 66, "aralykl" should read --aralkyl--.

Claim 5, Column 9, line 11, "$C_1$-$C_6$" should read --$C_1$-$C_6$--.

Signed and Sealed this

Fifteenth Day of July, 1997

Attest:

BRUCE LEHMAN

*Attesting Officer*     *Commissioner of Patents and Trademarks*